United States Patent
Mikoshiba et al.

[11] Patent Number: 5,093,573
[45] Date of Patent: Mar. 3, 1992

[54] REFLECTION ELECTRON DIFFRACTOMETER AND METHOD FOR OBSERVING MICROSCOPIC SURFACE STRUCTURE

[76] Inventors: Nobuo Mikoshiba, Yagiyamahon-cho Taihaku-ku; Tadashiro Ohmi, Komegafukuro Aoba-ku; Kazuo Tsubouchi, Hitokita Iaihaku-ku; Kazuya Masu, Mikamine Taihaku-ku, all of Sendani, Japan

[21] Appl. No.: 532,422

[22] Filed: Jun. 4, 1990

[51] Int. Cl.⁵ .......................................... H01J 37/29
[52] U.S. Cl. .................................. 250/310; 250/307
[58] Field of Search .............. 250/307, 310, 311, 397, 250/442.1

[56] References Cited
U.S. PATENT DOCUMENTS

| | | | |
|---|---|---|---|
| 4,068,123 | 1/1978 | Kokubo | 250/310 |
| 4,233,509 | 11/1980 | Tamura et al. | 250/310 |
| 4,438,332 | 3/1984 | Lichtenegger | 250/310 |
| 4,843,029 | 6/1989 | Joyce et al. | 437/80 |
| 4,855,013 | 8/1989 | Ohta et al. | 437/936 |
| 4,912,313 | 3/1990 | Kato et al. | 250/307 |
| 5,010,250 | 4/1991 | Elsayed-Ali | 250/310 |

*Primary Examiner*—Bruce C. Anderson
*Attorney, Agent, or Firm*—Armstrong, Nikaido, Marmelstein, Kubovcik & Murray

[57] ABSTRACT

An improved RHEED apparatus and a method for observing step-like surface irregularities of a sample by the use of the improved RHEED apparatus.

2 Claims, 5 Drawing Sheets

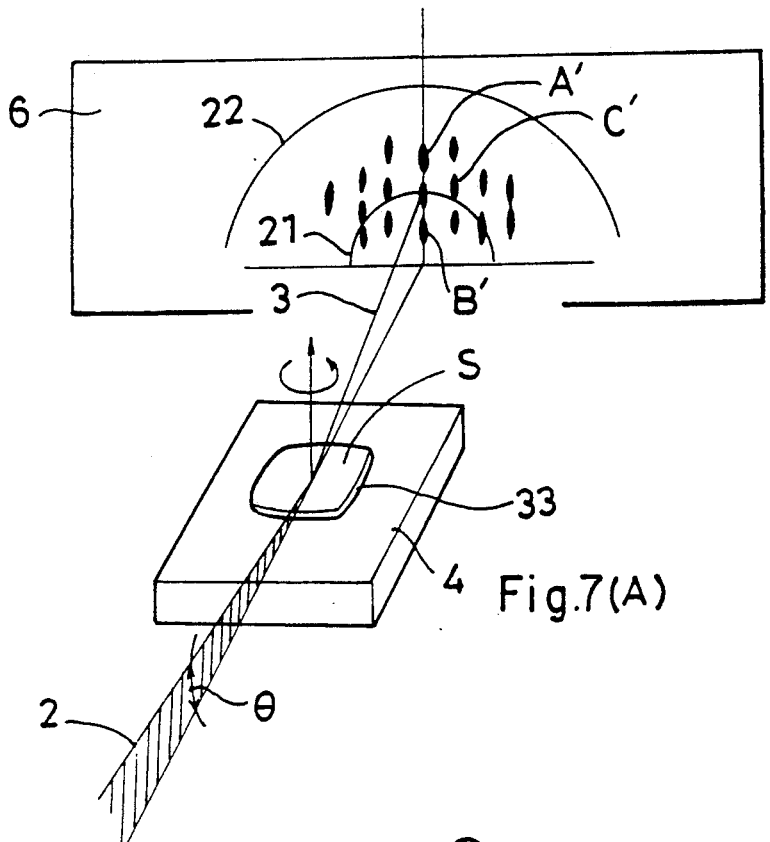
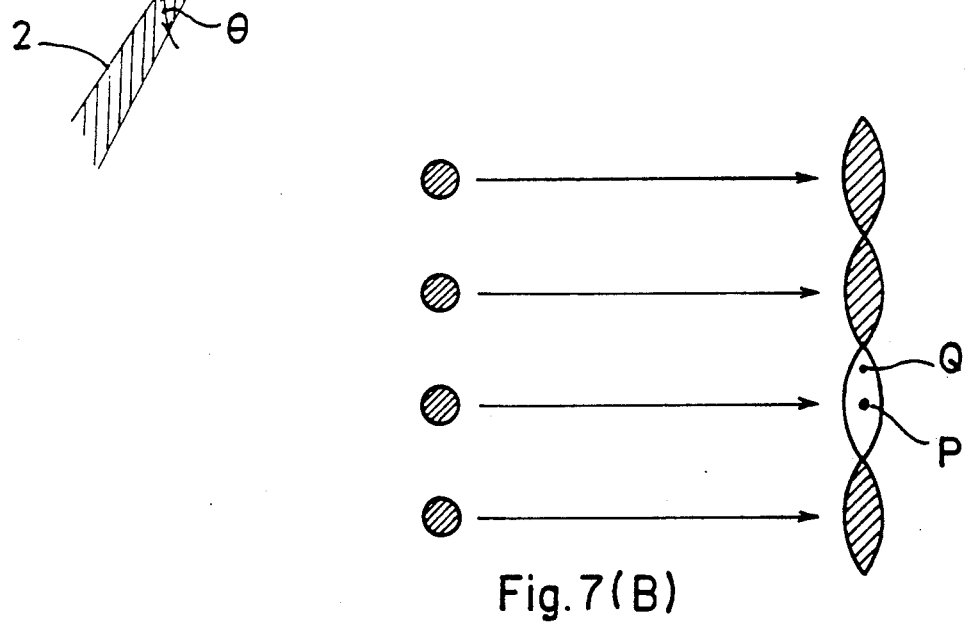
Fig.7(A)
Fig.7(B)

REFLECTION ELECTRON DIFFRACTOMETER AND METHOD FOR OBSERVING MICROSCOPIC SURFACE STRUCTURE

BACKGROUND OF THE INVENTION

The present invention relates to an improved reflection electron diffractometer and a method for observing microscopic surface structures of a sample by means of reflection electron diffractometry.

The growing demand for higher quality integrated circuits necessitates a more advanced technology of precisely controlling the deposition or expitaxial growth of microscopic metallic films forming an integrated circuit.

For example, micron-sized narrow aluminum or aluminum alloy current-lead films wired in an integrated circuit, if they have their crystalline directions not aligned properly, are liable to get snapped due to the electromigration effected in the films when large currents flow through them or due to the stress-migration originated from stresses often concentrated at the crystal boundaries of the substrate on which are laid the films. In order to check and evaluate integrated-circuits just formed on a wafer and also to establish the conditions that make it possible to produce integrated circuits made free from such trouble, it is necessary to provide with any convenient means for easily observing and evaluating the microscopic inner crystalline structure of the current-lead films and the micron-order near-surface fine crystalline structure of the substrate on which the current-lead films are laid. Obviously, a usual X-ray or electron diffractometer, which uses an X-ray or electron beam with a diameter ranging roughly from 0.1 to 1 mm, is useless for the purpose, because the beam diameter is too large to give microscopic information contained in a region of the order of micron, only capable of giving some information averaged over the region.

A transmission type electron microscope, which makes microscopic crystalline observation possible, is not practical either, because it is inevitably accompanied by a troublesome process of preparing a sample piece taken out from a wafer on which are formed integrated circuits. Further, the necessity of sample piece to be taken out makes it impossible to evaluate the films and substrate under the condition that the wafer with integrated circuits already formed thereon should be kept as it is.

Alternatively, a reflection high energy electron diffraction (RHEED) method may seem applicable to the examination of near-surface crystalline structure. However, this method is not applicable either, because it also gives only some averaged information contained in a wide region spreading over 0.1 to several millimeters in accordance with the diameter of the electron beam used. As to the problem of electron beam diameter, a microprobe RHEED method may be considered to be only a possible means for examining microscopic crystalline structure. Since this method uses as thin a beam as the order of 0.1 micrometer, the size distribution of crystallites is obtained by analyzing the intensity variation of a specific diffraction spot, the intensity variation being observed with the beam made to scan the surface of an objective of obsevation. However, as to the information on the directions of crystallites, the microprobe RHEED method gives only the information on the specific crystallite-faces having a common direction with respect to the incident electron beam, failing to give any information as to the directional distribution of the faces vertical to the above specific crystallite-faces.

As is briefed above, any conventional apparatus or method for crystallographic analysis cannot give enough information to evaluate the microscopic crystalline structure in the films formed on a substrate and in a micron-order shallow depth of the substrate.

In addition to the above-mentioned problems, there is a further need for a method of precisely observing one-atomic layer unevenness on the surface of a semiconductor substrate.

For instance, when gallium arsenide is to be epitaxially deposited on a silicon substrate whose atomic distance is different from that of gallium arsenide, a formed long-ranging gallium arsenide film is often accompanied by lattice defects. Therefore is desirable to make the silicon substrate uneven-surfaced so as to form one-atomic layer steps having their treads sized so as not to be too wide to make gallium arsenide films deposited thereon substantially free from lattice defects. In another case where a super high speed device is manufactured, the silicon substrate is, to the contrary, desired to be as smooth as possible, because even a one-atomic layer step causes electron mobility to be lowered.

To evaluate the smoothness (or unevenness) of the order of one-atomic layer, the previously mentioned microprobe RHEED method is found applicable. However, this method can provide only a general concept about the distribution of surface steps, failing to give the exact information on the surface steps or smoothness, because the method is not only barely capable of giving a low-contrast surface image on a CRT but also is lacking in a means for identifying a region being observed.

OBJECTS AND SUMMARY OF THE INVENTION

The present invention aims at resolving the above-discussed disadvantageous problems involved in observing the surface or near-surface microscopic crystalline structure of a sample by means of a conventional electron diffraction method, transmission type electron microscope or a microprobe RHEED, and makes it an object to provide an improved RHEED apparatus, which, can provide information on the three-dimensional directional relationships among the crystallites contained in the near-surface of a sample with an accuracy of the order of micrometer with the sample kept as it is, namely, without taking out from the sample such a sample piece as required for the electron microscope.

Another object of the present invention is to provide a method of electron-diffractometrically analyzing steps-like surface irregularities of a sample with an accuracy of one-atomic layer by using the improved RHEED apparatus.

To achieve the above objects the improved RHEED apparatus consists essentially of a beam source which emits as thin an electron beam as 0.1 micrometer, a goniometric sample holder for holding a sample to be irradiated by the electron beam, a fluorescent screen on which are projected electron beams diffracted by the sample, a plurality of displacable light guides for picking up light signals from the fluorescent screen, a photoelectric converting means for converting the light signals guided thereto by the light guides, an arithmetic means for performing various mathematical operations on the signals outputted from the photoelectric signal-conversion means, a CRT for displaying a signal outputted from the arithmetic means, and a means for making the electron beam scan the surface of the sample synchronously with a signal-sweeping operation of the CRT.

With the improved RHEED apparatus constituted as discussed above, the displaceable light guides and the arithmetic means make it possible, with the light guides positioned purposefully, to obtain not only mathematically processed intensities of the diffraction spots lighting on the fluorescent screen, but also a difference in brightness between different points within one diffraction spot. These characteristic functions enable the apparatus to display, on the CRT, not only the information on the three-dimensional alignment of the crystallites contained in the near-surface of a sample, but also a pattern of the one-atomic layer steps-like surface unevenness of a sample.

BRIEF DESCRIPTION OF THE DRAWINGS

The present invention is described in further detail in the following in accordance with the accompanying drawings, in which:

FIG. 7(A) schematically shows diffraction spots obtained from a sample having on its surface step-like unevenness;

FIG. 7(B) illustrates the positioning of light guides for obtaining a clear CRT display pattern of the step-like unevenness on the surface of a sample.

DETAILED DESCRIPTION OF THE INVENTION

Figure 1:
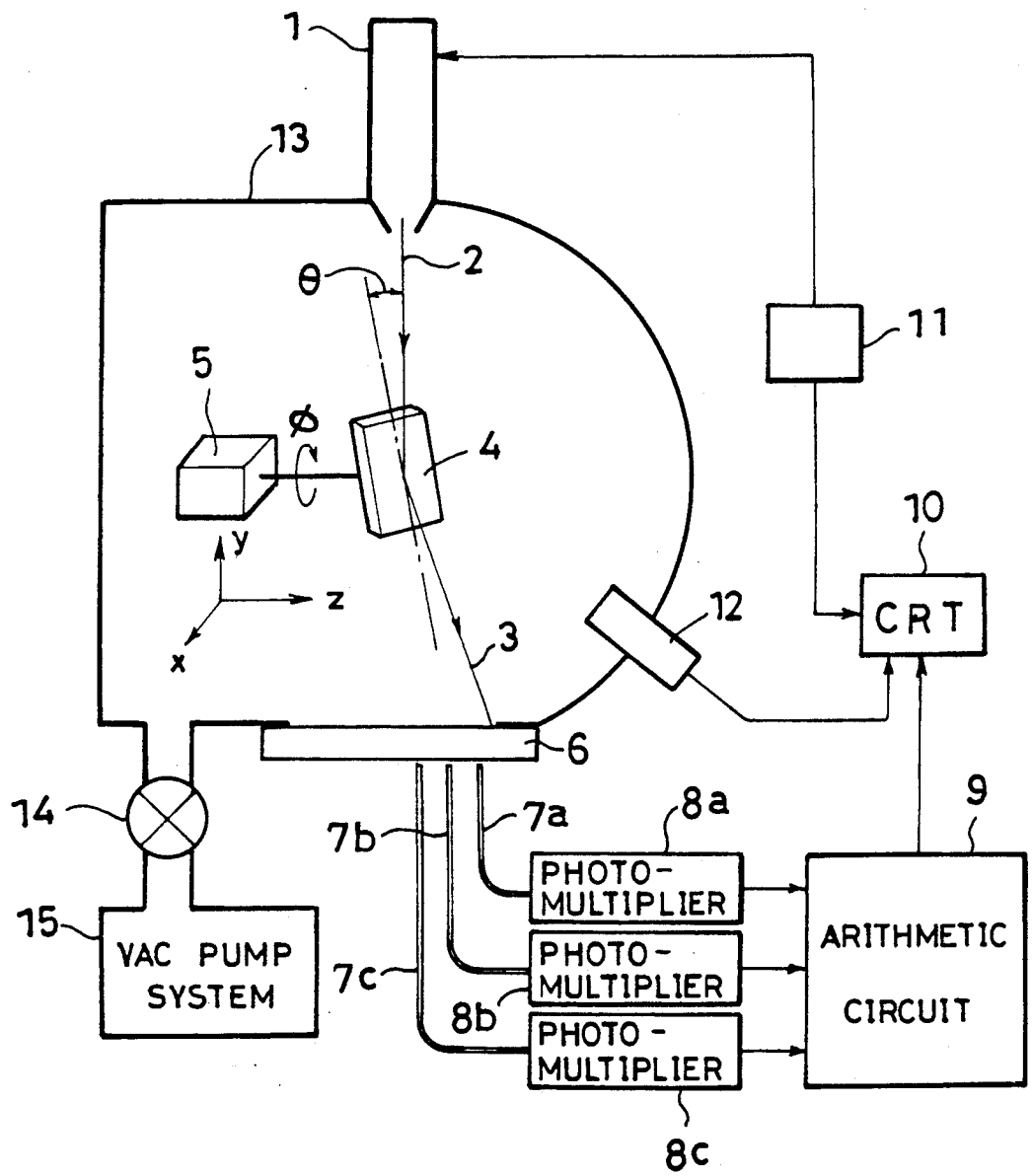
FIG. 1 schematically shows the constitution of an exemplified RHEED apparatus according to the present invention.

Referring to FIG. 1, which schematically shows the fundamental constitution of an example of the improved RHEED apparatus, an electron gun 1 emits an electron beam 2 to irradiate the surface of a sample 4 at as small an irradiating angle $\theta$ as 2 to 3 degrees. Preferably, the electron beam 2 is not larger than 0.1 micrometer in diameter and not larger than $1.5 \times 10^{-3}$ radian in beam converging angle. The electron gun 1 is provided with a means to make the electron beam 2 scan the surface of the sample 4. The electron beam 2 is diffracted by the sample 4, and diffracted electron beams 3 are projected on a fluorescent screen 6 to give diffraction spots thereon. The sample 4 is mounted on a goniometric sample holder 5 so that the relative direction of the electron beam 2 to the sample 4 can be varied with respect both to the irradiation angle $\theta$ and to an angle $\phi$ of rotation around the point of beam irradiation. The the goniometric sample holder 5 is further provided with a displacement mechanism (not shown) for displacing the sample holder 5 itself in parallel to x, y and z-directions as defined in the figure. A reference numeral 12 represents a detector for detecting not the diffracted electrons, but the secondary electrons emitted from the sample. The detector 12 is for properly positioning the sample. The above constituents, which are basically the same as those of a conventional microprobe RHEED apparatus, is of course devised to function in a vacuum space enclosed by a vacuum chamber 13, which is evacuated by a vacuum-pumping system 15 through a valve 14. In addition to the above constitution, the present apparatus is further provided with three displaceable light guides 7a, 7b and 7c made of optical fibers, three photomultipliers 8a, 8b and 8c, an arithmetic circuit 9 and a CRT 10, which is made, by a timing circuit 11, to operate synchronously with the scanning operation of the electron beam 2. The displaceable light guides 7a, 7b and 7c have their tips purposefully positioned on the fluorescent screen 6 to pick up light signals from electron diffraction spots on the screen 6 or from the background of the screen 6. The light signals picked up by the light guides 7a, 7b and 7c are converted to corresponding electric signals by the photomultipliers 8a, 8b and 8c, and then displayed on the CRT 10 after being mathematically processed by the arithmetic circuit 9 or as they are, namely, without being processed.

Figure 2:
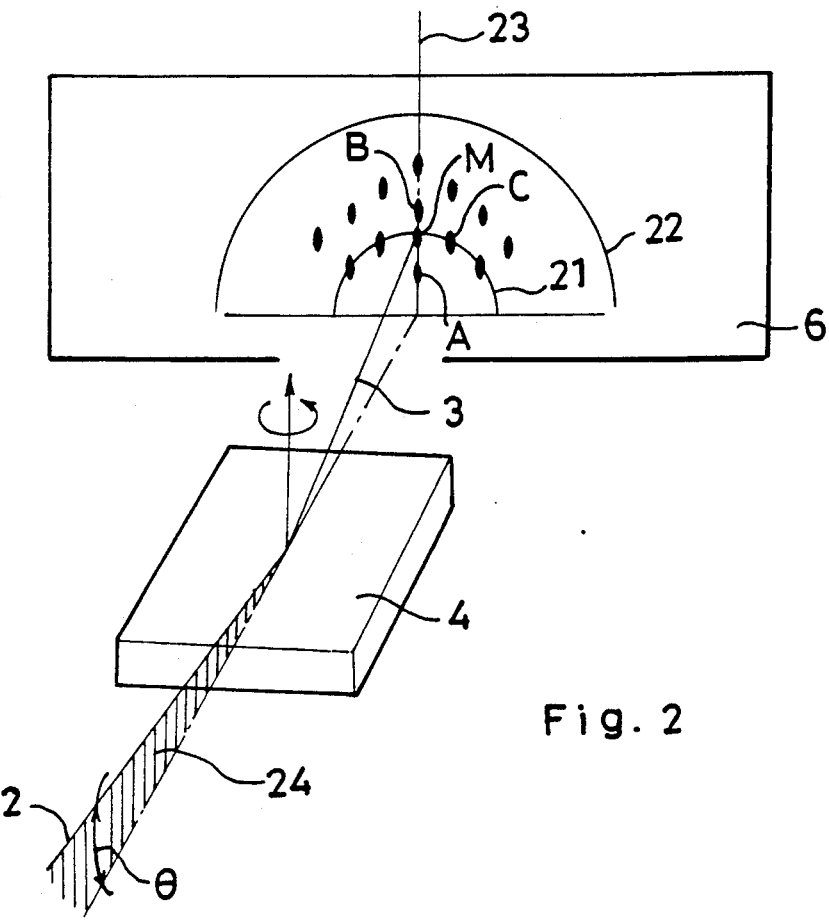
FIG. 2 shows the relation between a sample irradiated by an incident electron beam and an obtained electron diffraction pattern.
Figure 3:
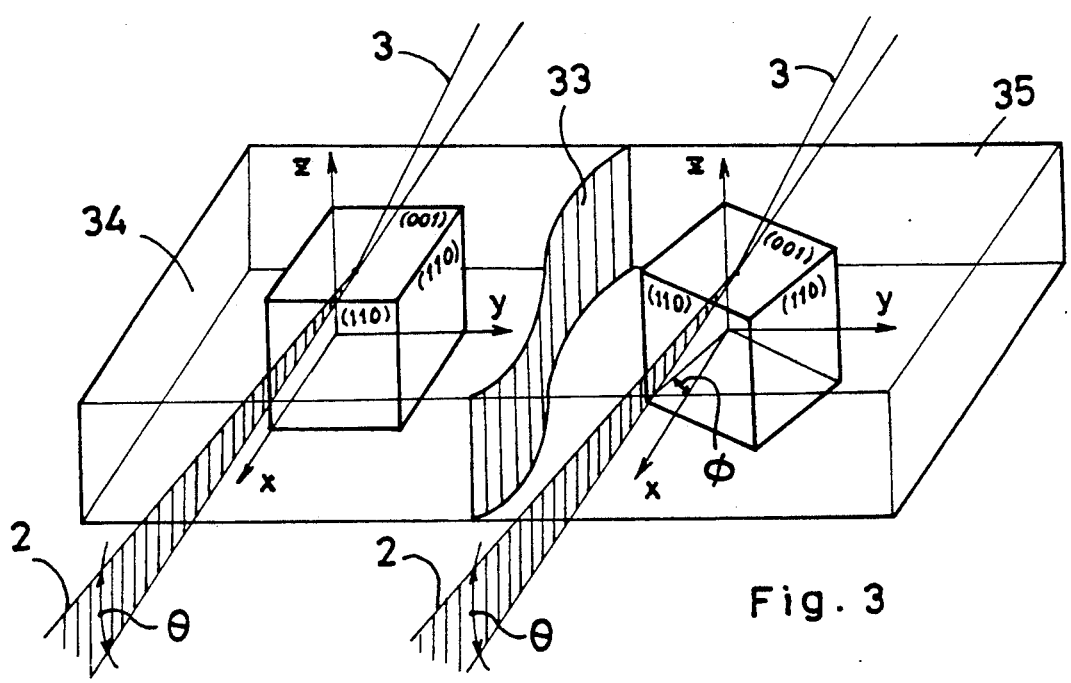
FIG. 3 schematically illustrates the principle of determining the directional relation of differently directed crystallites belonging to different crystalline zones.

In such a whole constitution of the apparatus, the sample 4, which is irradiated by an electron beam 2 at an irradiation angle $\theta$, diffracts the incident beam, giving on the fluorescent screen 6 some diffraction spots M, A, B, C and others as shown in FIG. 2. To make the description simple, suppose that FIG. 2 represents the diffraction pattern obtained when the incident electron beam 2 irradiates a region in which all the near-surface crystallites are directed in the same direction with their lattice planes (001) made parallel with the surface of the sample 4 (refer to the part indicated by a reference numeral 34 in FIG. 3), then the (001) planes and their equivalents are represented by the diffraction spots A and B located on the imaginary line 23 formed at the intersection of the screen 6 and a plane 24 being vertical to the surface of the sample 4 with the incident electron beam 2 contained, while the diffraction spots C corresponds to another lattice planes (110) vertical to the (001) planes. Incidentally, the spot M represents the direct reflection of the incident electron beam 2 by the surface of the sample 4. However, if the incident electron beam 2, which scans the surface of the sample 4, enters into another region in which the (110) planes rotate by an angle $\phi$ with the (001) planes still kept parallel with the surface of the sample 4 (refer to the part indicated by a reference numeral 35 in FIG. 3), the diffraction spot C moves to a different position and often goes out from the screen 6, while the spots A and B remain unmoved. In this case, with the sample itself rotated by an angle $-\phi$, the spot C returns to the original position, and thus the rotation angle $\phi$ can be determined. Though the above description on the principle of the invention is limited to the case where the (001) planes are parallel with the sample surface for the purpose of making the description simple, it will be obvious that the improved RHEED apparatus shown in FIG. 1 makes it possible to analyze the three-dimensional crystalline structure in the near-surface of any sample of a crystalline substance, such as a semiconductor-substrate and a semiconductor wafer on which integrated circuits are formed.

In the following is described a method of displaying on the CRT 10 the near-surface crystalline structure of a sample.

Figure 4:
FIG. 4 are a CRT display pattern made by secondary electrons emitted from a sample scanned by an incident electron beam.

In the first place a sample is properly positioned by displaying on the CRT 10 a pattern obtained from the secondary electrons detected by the detector 12. The pattern, which is given in FIG. 4, shows a marker m provided on the sample and dot-like images corresponding to the microscopic surface flaws.

Figure 5A:
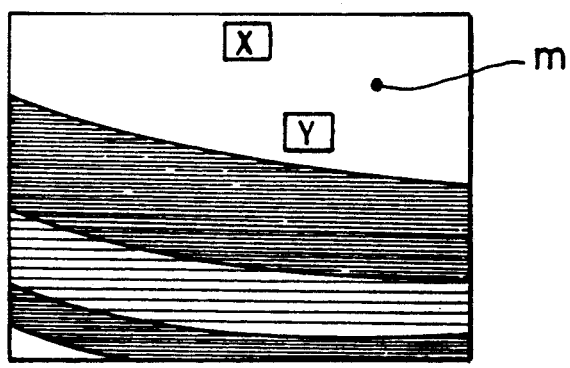
FIGS. 5(A) and 5(B) are CRT display patterns made by different diffraction spots obtained with an incident electron beam made to scan the surface of the same sample that is mentioned in the description of FIG. 4.

Then, with a diffraction pattern (similar to that shown in FIG. 2) obtained on the screen 6, put one of the light guides 7a, 7b and 7c on the diffraction spot A, and the pattern as shown in FIG. 5(A) is displayed on the CRT 10. When the incident electron beam is scanning the region where all the crystallites have their (001) planes kept parallel with the sample surface, the corresponding area on the CRT screen is bright as indicated by X and Y in FIG. 5(A).

Figure 5B:
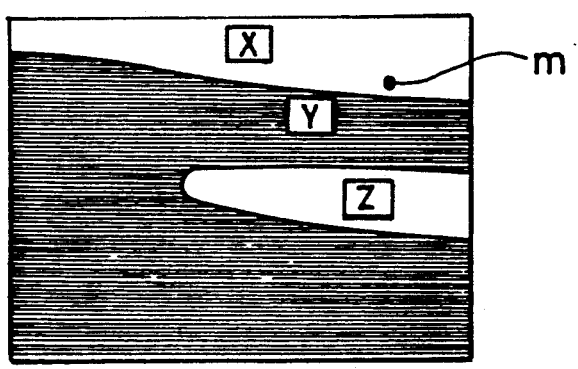

If one of the light guides is put on the diffraction spot C, a display pattern as shown in FIG. 5(B) is obtained on the CRT 10. In the pattern, bright areas X and Z represent such a region as indicated by 34 in FIG. 3.

Figure 6A:
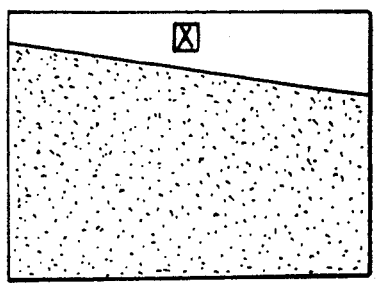
FIGS. 6(A) and 6(B) are CRT display patterns obtained by performing predetermined arithmetic operations on the different diffraction spots mentioned in the description of FIGS. 5(A) and 5(B)
Figure 6B:
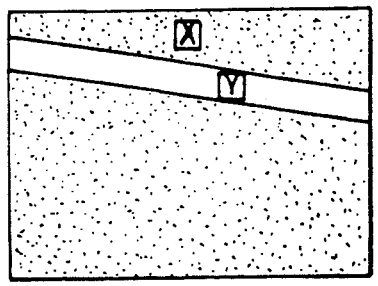

With two of the light guides put on the spots A and C, respectively, and with the arithmetic circuit 9 made to sum the intensities of spots A and B, the CRT displays a pattern as shown in FIG. 6(A). With the two light guides still kept at the spots A and C, respectively, and with the arithmetic circuit 9 made to substract the intensity of the spot C from that of the spot A, a display pattern as shown in FIG. 6(B) is obtained.

Further, a method of observing the atomic order step-like unevenness of the sample surface is described in the following.

As is shown in FIG. 7(A), if a sample 4 has one-atomic layer step-like unevennness S on its surface, the diffraction spots are weakened and elongated vertically as best shown in FIG. 7(B). This tendency is remarkable particularly when the direction of the incident electron beam 2 is perpendicular to the step 33. Of course, when the incident beam 2 is scanning the flat portion of the step 33, the diffraction spots are the same as those seen in FIG. 2.

Figure 8A:
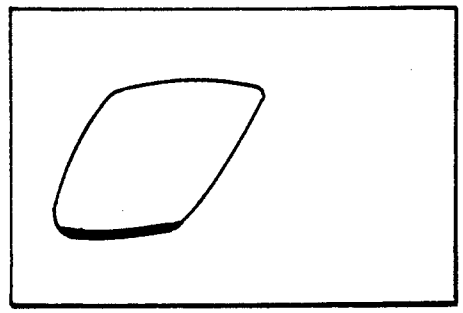
FIGS. 8(A), 8(B) and 8(C) are CRT display patterns showing the same step-like unevenness on the surface of a sample in various contrasts.
Figure 8B:
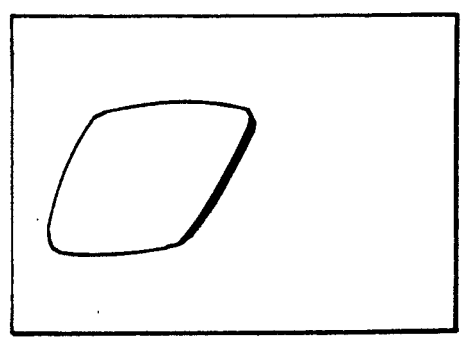
Figure 8C:
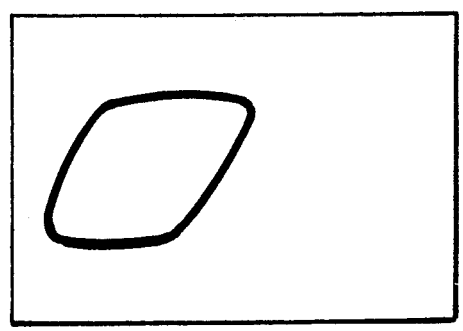

In this case, one light guide is put at the central point P of a prolonged spot A and another light guide is put on a point Q a little separated from the point P. Then, the intensity at the point Q is subtracted from the intensity at the point P. The obtained CRT display pattern has a good contrast, as shown in FIG. 8(A), at the portion corresponding to the step 33, particularly at the edge perpendicular to the incident electron beam. On the other hand if a similar arithmetic operation is made as to the intensity at the point P and the intensity of the spot C, the edge portion parallel with the direction of the incident beam has a good contrast as shown in FIG. 8(B). Therefore, by performing the similar arithmetic operation as to the points P, Q and the spot C, the whole periphery of the step has a good contrast as shown in FIG. 8(C).

Further, with an evaporation source, a heater, an etching means and the like provided within the vacuum space enclosed by a vacuum chamber 13, the above described observation can be made on real time while processing a semiconductor device.

While the invention has been particularly shown and described in reference to preferred embodiments thereof, it will be understood by those skilled in the art that changes in form and details may be made therein without departing from the spirit and scope of the invention.

We claim:

1. A reflection high energy electron diffraction apparatus comprising:
    an electron beam source means for emitting a sample-irradiating electron beam with a diameter of about 0.1 micro-meter, said electron beam source being provided with means capable of having said electron beam scan a sample;
    a goniometric sample holder means for holding said sample;
    a flourescent screen for receiving diffracted electron beams from said sample;
    a plurality of displaceable light guide means for receiving light signals from said fluorescent screen;
    a photoelectric converting means connected to said light guide means for converting said light signals to electrical signals;
    arithmetic means for computing a mathematical linear combination of said electrical signals; and
    a display means for displaying a crystallographical surface aspect of said sample according to an output from said arithmetic means, with said sample-irradiating electron beam made to scan said sample.

2. A method of observing step-like unevenness on a surface of a sample by using an apparatus having an electron beam source which emits a sample-irradiating electron beam with a diameter of about 0.1 micro-meter and scans a sample; a goniometric sample holder which holds said sample; a fluorescent screen for receiving diffracted electron beams from said sample; a plurality of displaceable light guides which receive light signals from said fluorescent screen; a photoelectric converter connected to said light guides which converts said light signals to electrical signals; arithmetic device which computes a mathematical linear combination of said electrical signals; and a display which displays a crystallographical surface aspect of said sample according to an output from said arithmetic device, said method comrpising the steps of:
    scanning said sample with an electron beam;
    picking up light intensities at different points in the same diffraction spot or light intensities at different diffraction spots of said sample, said different points or said different diffraction spots having their luminosities mutually inverted when sample-scanning electron beam sweeps at riser portions of said step-like unevenness formed on the surface of said sample; and
    perfoming an arithmetic operation based on said light intensities.

* * * * *

UNITED STATES PATENT AND TRADEMARK OFFICE
CERTIFICATE OF CORRECTION

PATENT NO. : 5,093,573
DATED : March 3, 1992
INVENTOR(S) : Nobuo Mikoshiba et al It is certified that error appears in the above-identified patent and that said Letters Patent is hereby corrected as shown below:

Title page, Item [76], second line, "Tadashiro Ohmi" should read -- Tadahiro Ohmi --.

Title page, Item [76], last line, "Sendani, Japan" should read -- Sendai, Japan --.

Signed and Sealed this

Twenty-second Day of June, 1993

Attest:

MICHAEL K. KIRK

*Attesting Officer*     *Acting Commissioner of Patents and Trademarks*

UNITED STATES PATENT AND TRADEMARK OFFICE
CERTIFICATE OF CORRECTION

PATENT NO. : 5,093,573

DATED : March 3, 1992

INVENTOR(S) : Mikoshiba, et al

It is certified that error appears in the above-identified patent and that said Letters Patent is hereby corrected as shown below:

On the title page: Item [76]: Inventor, "Hitokita Iaihaku-ku" should read --Hitokita Taihaku-ku--.

Signed and Sealed this

Twenty-first Day of September, 1993

Attest:

BRUCE LEHMAN

Attesting Officer     Commissioner of Patents and Trademarks